United States Patent [19]
Classon et al.

[11] Patent Number: 5,567,309
[45] Date of Patent: Oct. 22, 1996

[54] SELF-FILTRATION CAP

[75] Inventors: Robert J. Classon, Earleville, Md.; Karl N. Caldwell, Norcross; Louis O. Leazenbee, Lawrenceville, both of Ga.

[73] Assignee: Alcott Chromatography, Inc., Norcross, Ga.

[21] Appl. No.: 196,854

[22] Filed: Feb. 14, 1994

(Under 37 CFR 1.47)

[51] Int. Cl.$^6$ ........................................ B01D 33/00
[52] U.S. Cl. .................. 210/233; 210/244; 210/359; 210/416.1; 210/455; 210/484; 210/495; 422/100; 422/101
[58] Field of Search ..................... 210/233, 244, 210/359, 416.1, 455, 321.67, 321.75, 484, 495; 73/863.23; 422/100, 101

[56] References Cited

U.S. PATENT DOCUMENTS

| | | | |
|---|---|---|---|
| 3,846,077 | 11/1974 | Ohringer | 23/259 |
| 3,918,913 | 11/1975 | Stevenson et al. | 23/259 |
| 3,932,277 | 1/1976 | McDermott et al. | 210/77 |
| 3,955,423 | 5/1976 | Ohringer | 73/425.4 |
| 3,962,085 | 6/1976 | Liston et al. | 210/131 |
| 4,644,807 | 2/1987 | Mar | 73/864.62 |
| 4,891,134 | 1/1990 | Vcelka | 210/359 |
| 4,895,808 | 1/1990 | Romer | 436/178 |
| 4,973,450 | 11/1990 | Schlüter | 422/101 |

OTHER PUBLICATIONS

The World of EM Science/Hitachi Presents the Model 655A–40 Autosampler for HPLC, 1985.
Automatic Liquid Sample Processor for Large Series of Complex Analyses, Oct. 1987.
Micromeritics 725 AutoInjector, Automate Your HPLC Analyses With The World's Most Widely Accepted Automatic Sample Injector.
ETP/KORTEC HPLC Autosampler Model K65B, Apr. 1986.
Direct Scientific—Spring 1987 Lab Products.
Waters HPLC Automation System, Sep. 1981.
Instruments from MERCK, The 655A–40 Autosampler.
Hewlett Packard, The HP1090 Series M Liquid Chromatographs, Oct. 1985.

*Primary Examiner*—Matthew O. Savage
*Attorney, Agent, or Firm*—Jones & Askew

[57] ABSTRACT

An improved filtration device capable of filtering and storing liquid which can then be removed from the device for analysis. A top cap is placed over a filter cap such that a seal is created between these two caps. The filter cap has an opening on its bottom end which is covered by a filter membrane. A storage reservoir is created in the device when the top cap and the filter cap are sealed together. These caps are then slidably received by a vial containing unfiltered sample such that a seal is formed with the interior wall of the vial and the outer wall of the top cap. A needle with a needle housing pierces the top cap and forces the device downward which directs the sample in the vial through the filter on the filter cap and into a storage reservoir to be removed through the needle.

17 Claims, 5 Drawing Sheets

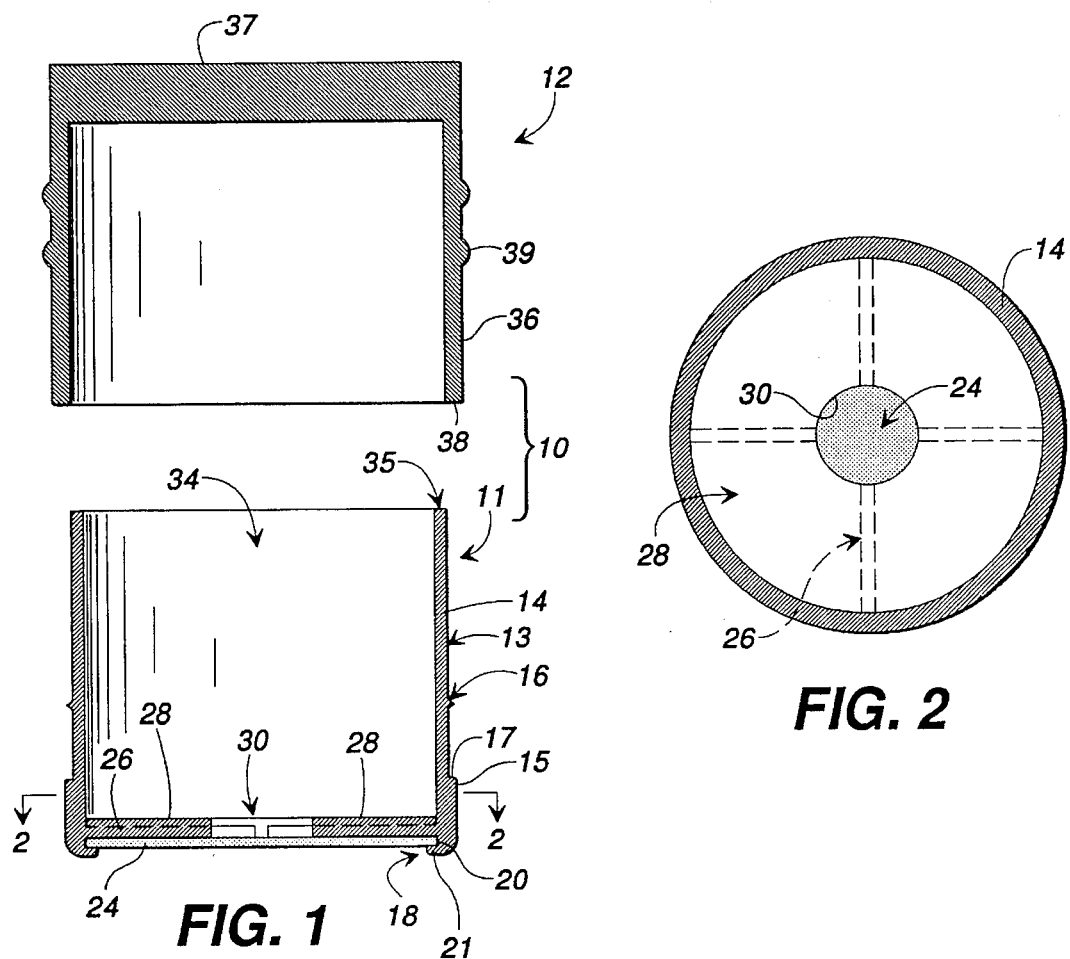
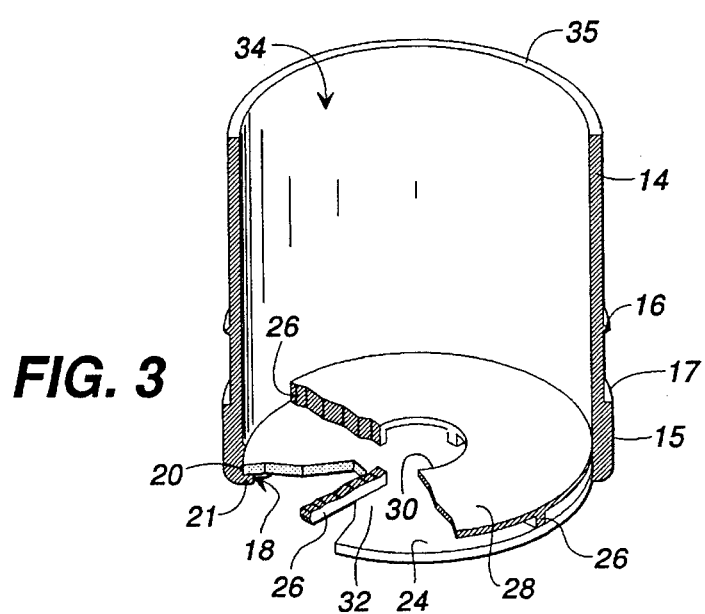

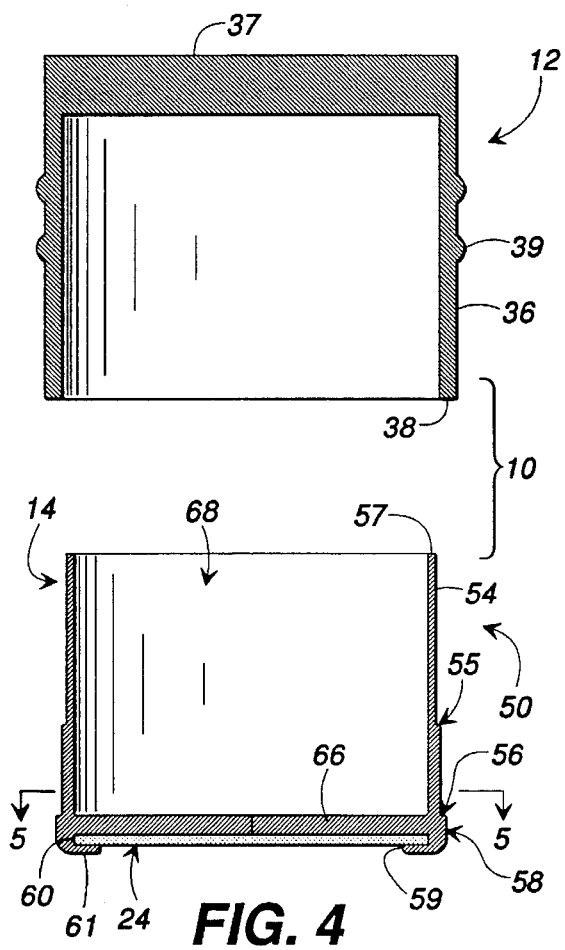
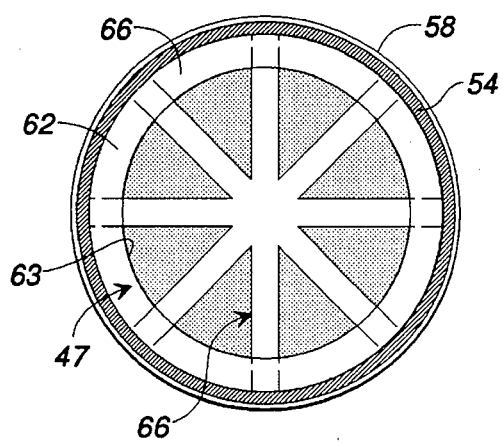
FIG. 5
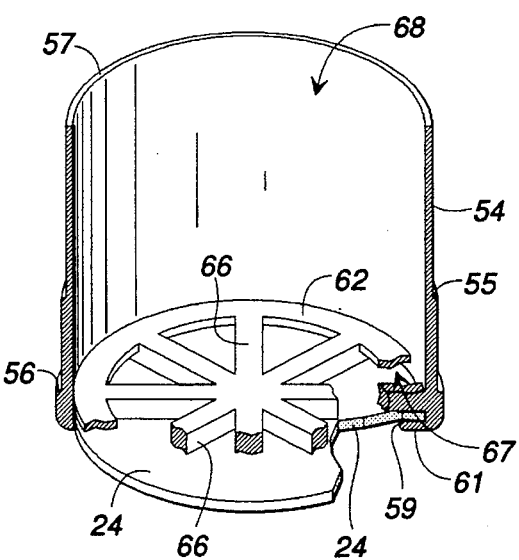
FIG. 6

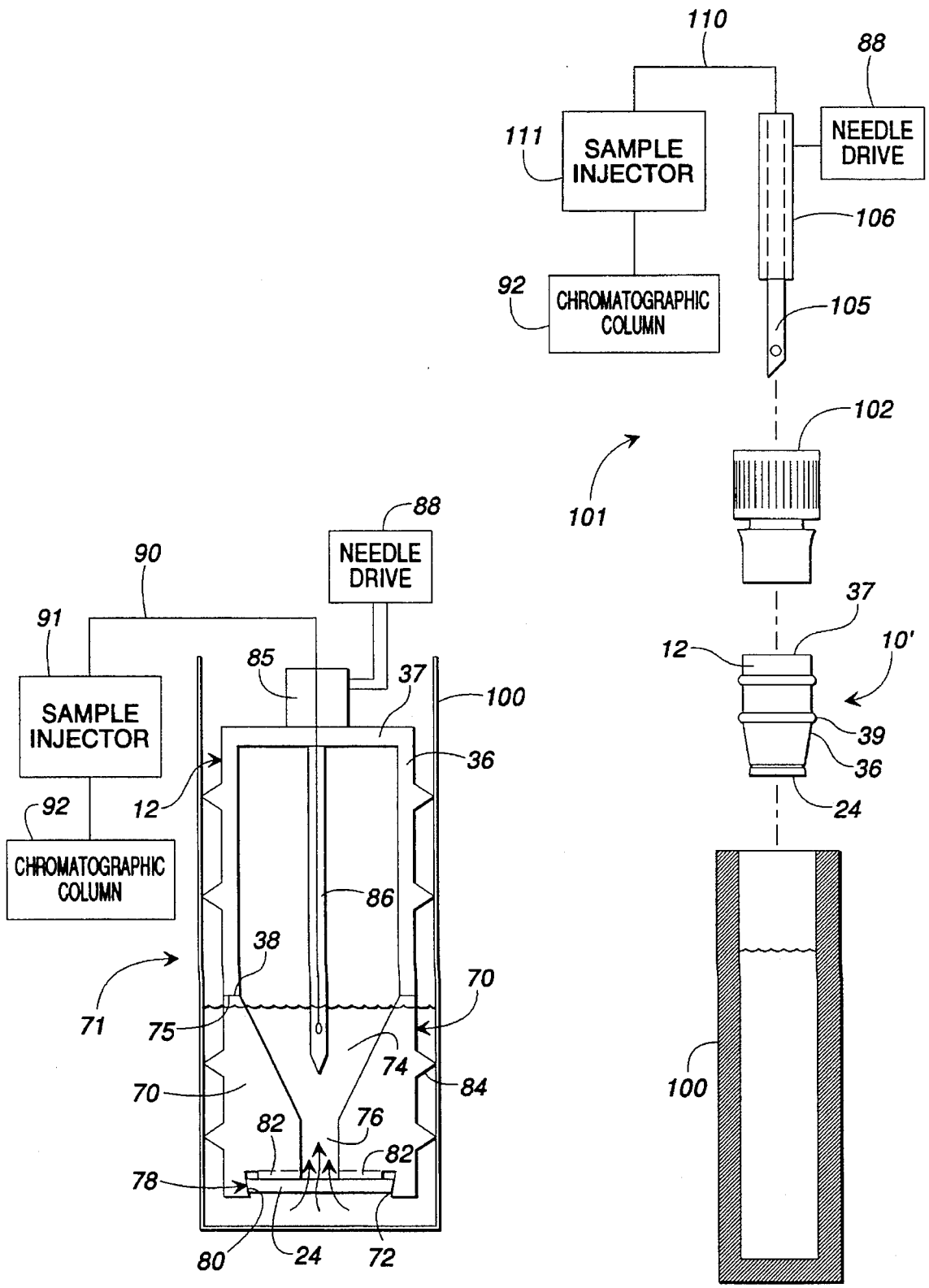

SELF-FILTRATION CAP

TECHNICAL FIELD

This invention relates to a filtration device and, in particular, to a self-filtration cap which is designed such that the cap is capable of filtering and storing liquid which can be removed from the cap for any of several types of analyses, such as the analysis required to perform liquid chromatography.

BACKGROUND OF THE INVENTION

Liquid chromatography involves a process for separating various components of liquids in order to analyze the chemical content of the liquid. An amount of solute sample containing unknown components to be analyzed is injected into a chromatographic column. A carrier fluid is then introduced into the column under pressure, and causes the components of the sample to travel through the column at slightly different velocities. This results in the formation of essentially pure fractions of the components in bands or zones. The identity of the chemical components can be determined from measuring the separated bands using a spectrophotometer or other identifying device. Such chromatographic analyses are typically performed under high pressure conditions, usually 1,000 psig or higher, for greater speed.

The sample solution may be delivered to a chromatograph or other analyzer using a sampler-injector or autosampler. One type, such as shown in U.S. Pat. No. 3,918,913, delivers the sample by positive displacement of the sample from a vial to the analyzer. The sample is placed in a vial which is then closed by a plastic cap. At the proper time, a hollow needle is driven through a septum in the plastic cap, and a collar surrounding the needle forces the cap into the vial in piston-like fashion, pressurizing its contents and forcing the sample liquid through the needle and along a liquid line to the analyzer. Another type of sample delivery system uses negative displacement; for example, the sample may be withdrawn by a syringe. This method may be advantageous when only a small amount of sample is available.

Prior to injecting a sample into a chromatographic column for analysis, it is desirable to filter the sample to remove any particulate matter or other solid material which may be in the sample. However, filtration generally results in the loss of some of the sample within the filter material. If the sample is costly or available in very small amounts, it may be necessary or desirable to be able to conduct chromatographic analysis using a small amount of the sample, for example less than 1,000 microliters. It is sometimes necessary to use as little as one microliter drawn from a total volume of five microliters. Furthermore, a filtration step takes time, and can slow down total analysis time. Therefore, filtration should be highly efficient in order to minimize delays and loss of sample. Prior filtration devices which have been designed and used for filtering samples prior to chromatographic analysis have demonstrated problems in effectively and efficiently preparing a filtered sample in an amount sufficient for chromatographic analysis.

Prior manual sample filtration devices include syringes with filters mounted at the end of the syringe. The sample would be injected into a vial as it was being filtered, and then the vial could be used in an autosampler. Manual piston-type filtration devices are also known in the art, for example as shown in U.S. Pat. Nos. 3,846,077 and 3,955,423 issued to Ohringer, 4,891,134 issued to Vcelka, 4,895,808 issued to Romer, and 3,962,085 issued to Liston. If any such devices were used to prepare a sample for chromatographic analysis, it would be necessary to transfer the sample to an injection device. Some of the above prior art devices are open tubes which provide no protection against contamination of the sample between filtration and transfer. Others provide a removable cover, but the process of uncovering the sample and manually pouring it introduces the opportunity for human error or sample contamination. Labor costs are also higher when filtration and transfer are conducted manually. Inefficiencies increase if the device is reusable rather than disposable after a single use.

Therefore, it is highly desirable to filter the sample as part of the operation of an autosampler which injects the sample into an analyzer. U.S. Pat. No. 4,644,807, issued to Mar, discloses a sample delivery apparatus for delivering samples of liquid to chromatographic columns. A special sampling tip, designed specifically for use in the Mar device, fits into a recess in a plunger that is slidably mounted in a vial containing the sample. The special sampling tip is moved downward to force the plunger into the vial and thereby force the sample through a filter mounted in the plunger into the sampling tip. One problem with the Mar device is that only the porous filter material protects the sample from the environment while awaiting operation of the sampling tip. Gaseous contaminants might penetrate the filter, or solid particles might collect on the filter and be carried to the analyzer. For the same reason, the Mar device is not suitable for use with organic samples, which can evaporate through the porous filter material.

Another problem with the Mar device, and many other filtration devices which are known in the art, has been the relatively large bulk and thickness of the filter medium itself. When a filter is positioned across a fluid path and will be subjected to fluid under pressure, as in the positive displacement Mar device, it must have sufficient internal strength to avoid bursting under the pressure. The required strength has often been provided by making the filter thicker. As noted above, retention of sample by the filter device excludes the retained portion of the sample from analysis. Thus, it may not be possible to use the Mar filtering device when only a small amount of unfiltered sample is available. Furthermore, providing space for a thick filter medium and its lengthy filtration path can cause an increase in the overall size of the filtration device.

The thick filter of Mar also presents a small surface area to the liquid on the upstream side of the filter. Therefore, more time or more pressure is required to force the entire sample through the filter, and the process is less efficient. It thus will be seen that although Mar provides filtration of sample during transfer of the sample to an analyzer, many problems remain affecting sample loss, sample protection, and filtration efficiency. Finally, the Mar device requires a gas-tight seal between the tip and plunger during proper operation. For example, if these parts are not precisely aligned, a leak may occur during sample transfer. Therefore, precision manufacturing and operation is required to obtain a gas-tight seal.

Thus, there has been a need in the art for a system of pre-filtering samples to be delivered automatically to an analyzer, which does not require a separate filtering step or manual handling of the sample, which does not require a thick filter element for structural integrity, which loses a minimum amount of sample within the filter medium, which filters liquid quickly without developing a large pressure build-up across the filter element, which does not require a gas-tight seal in use, and which consists of inexpensive, disposable components.

SUMMARY OF THE INVENTION

The present invention provides a filtration device and sample removal system which solves problems experienced in the prior art by providing a fully automatic, economical, single-use filtration device with a thin filter presenting a large surface area to the sample as well as good access for sample removal, without sample contamination or danger of filter breakdown, and with minimum sample retention in the filter.

The filtration device is generally defined by a housing which is fits into a vial and seals against the interior surface of the vial. A filter is provided on the lower or upstream end wall of the housing, and the sample passes through the filter and into the housing. The filter is supported against the pressure of the sample by support structure engaging a portion of the downstream surface of the filter. The downstream (or top) end wall of the housing is a septum or a plastic sheet which may be pierced by a needle of a sample delivery device. As a result of this structure, a thin microporous filter element, for example between 0.03 and 0.06 inches in thickness, is supported against collapsing or bursting under the pressure of the sample passing through it. The low-bulk filter minimizes sample loss.

In a preferred form, the housing comprises two parts: a filter receptacle including the upstream end wall and the filter, and a peripheral receptacle wall defining an upper facing shoulder and shaped to be received by the vial in liquid sealing engagement with the interior surface of the vial; and a cap including the downstream end wall and a peripheral cap wall defining a lower peripheral edge and also shaped to be received by the vial in liquid sealing engagement with the interior surface of the vial. The cap fits over the peripheral receptacle wall with the lower peripheral edge abutting the upper facing shoulder, such that the receptacle wall presses the cap wall against the interior surface of the vial to provide both an effectively sealed housing for the filtered sample and a liquid-tight seal with the vial.

In another embodiment of the invention, a partition is positioned within the housing to more distinctly divide the housing into two chambers, a filter chamber and a removal chamber. The partition also defines an opening to permit filtered liquid to pass from the filter chamber into the removal chamber. In a preferred form of this embodiment, the housing contains support ribs which are positioned to engage a portion of the downstream (or top) surface of the filter for support. The support ribs extend radially toward the center of the filter from a peripheral wall of the housing. A well may optionally be formed directly above the filtered liquid opening, having a cross sectional area smaller than the cross sectional area of the housing. Thus, a shallow filter chamber can collect sample passing efficiently through a large filter surface area, and then channel the sample into a deeper well into which an extraction needle can extend. This results in efficient delivery of small amounts of samples which would not fill the entire cross section of the housing to a sufficient depth.

According to another aspect of the invention, the filtration device forms a part of a sample removal and delivery system. The sample removal and delivery system includes a vial which contains liquid sample and which receives the filtration device. A needle mounted in a needle housing is also provided. A drive mechanism moves the needle and the needle housing down until the needle can pierce the septum or plastic cover and descend into the filtration device. The needle housing then engages the top of the filtration device and forces it down into the vial, forcing liquid through the filter and into the housing and into the needle.

It will be appreciated that in a positive displacement sample delivery system the volume of liquid to be filtered can be larger than the internal volume of the filtration device described above, because the liquid is forced up through the needle as filtration proceeds. With modifications described as follows, the filtration device of the present invention can also be used with negative displacement delivery of samples varying widely in sample volume.

Another embodiment of the sample removal and delivery system, is utilized with negative displacement sample delivery when the volume of sample exceeds the volume of the filtration device. In this embodiment, the septum or plastic cover on the downstream end wall of the filtration device discussed above is provided with vent holes so that liquid sample can flow into the housing through the filter until it fills the removal chamber, and through the holes and into the vial above the seal between the filtration device and the vial. The vial is preferably sealed with a protective septum or cover. The needle and the needle housing pierce and penetrate the septum or cover of the vial and descend into the vial. The needle then pierces the septum or plastic cover of the filtration device in the manner described above. The needle housing engages the top of the filtration device and pushes the filtration device down until the liquid sample is forced through the filter and into the housing of the filtration device, and on into the vial portion above the filtration device.

This alternate embodiment of a sample removal and delivery system may be used with negative displacement delivery of large samples, because the vent holes relieve pressure and allow the excess volume of sample to reenter the vial above the filtration device. Suction applied to the needle by the negative displacement syringe or pump may then withdraw virtually all of the sample down to the level of the filter.

Although the discussion above has focused on filtering sample prior to conducting chromatographic analysis, the present invention can be applied to other types of liquid chemical analysis which require filtering of liquid sample, including, but not limited to, ion chromatography, supercritical extraction, gas chromatography, and bio-medical applications such as plasma analysis.

Thus, it is an object of the present invention to provide an improved filtration device for use in a sample removal and delivery system.

It is a further object of the present invention to provide a filtration device and sample removal and delivery system which enable the use of a thin filter element such that the majority of sample coming in contact with the filter will exit the filter for analysis.

It is a further object of the present invention to provide a sample filtration device which protects a thin filter element against collapse.

It is a further object of the present invention to provide a sample filtration device which presents a large filtration surface area for efficient filtration.

It is a further object of the present invention to provide an economical sample filtration device which is disposable after one use.

It is a further object of the present invention to provide a filtration receptacle and sample removal and delivery system which can be completely automated such that no manual tasks need be performed.

It is a further object of the present invention to provide filtration devices for positive displacement sample delivery and for negative displacement sample delivery.

It is a further object of the present invention to provide a sample filtration device which can be used in a variety of different chemical analysis.

BRIEF DESCRIPTION OF THE DRAWINGS

FIG. 1 is an exploded side cross sectional view of a first embodiment of a two-part filtration device according to the present invention.

FIG. 2 is a top cross sectional view taken along line 2—2 of FIG. 1.

FIG. 3 is a pictorial view of the interior of the filter receptacle portion of the device of FIG. 1, with portions broken away to show detail.

FIG. 4 is an exploded side cross sectional view of a second embodiment of a two-part filtration device according to the present invention.

FIG. 5 is top cross sectional view taken along line 5—5 of FIG. 4.

FIG. 6 is a pictorial view of the interior of the filter receptacle portion of the device of FIG. 4, with portions broken away to show detail.

FIG. 8 is a side cross sectional view of a third embodiment of a two-part filtration device according to the present invention positioned within a vial, and showing diagramatically a needle drive mechanism and connection to an analyzer.

FIG. 9 is an exploded side cross sectional view of a sample removal and negative displacement delivery system according to the present invention which shows a needle drive mechanism and connection to an analyzer diagramatically.

DETAILED DESCRIPTION

Referring now in more detail to the drawings, in which like numerals refer to like parts throughout the several views, FIG. 1 shows a longitudinal cross section of the preferred embodiment of a filtering device 10 which filters sample and delivers it to an analyzer, or holds the filtered sample until it can be withdrawn for analysis. The filtering device 10 consists of two parts, a filter receptacle 11 and a cap 12 positioned directly above the filter receptacle 11.

Figure 7:
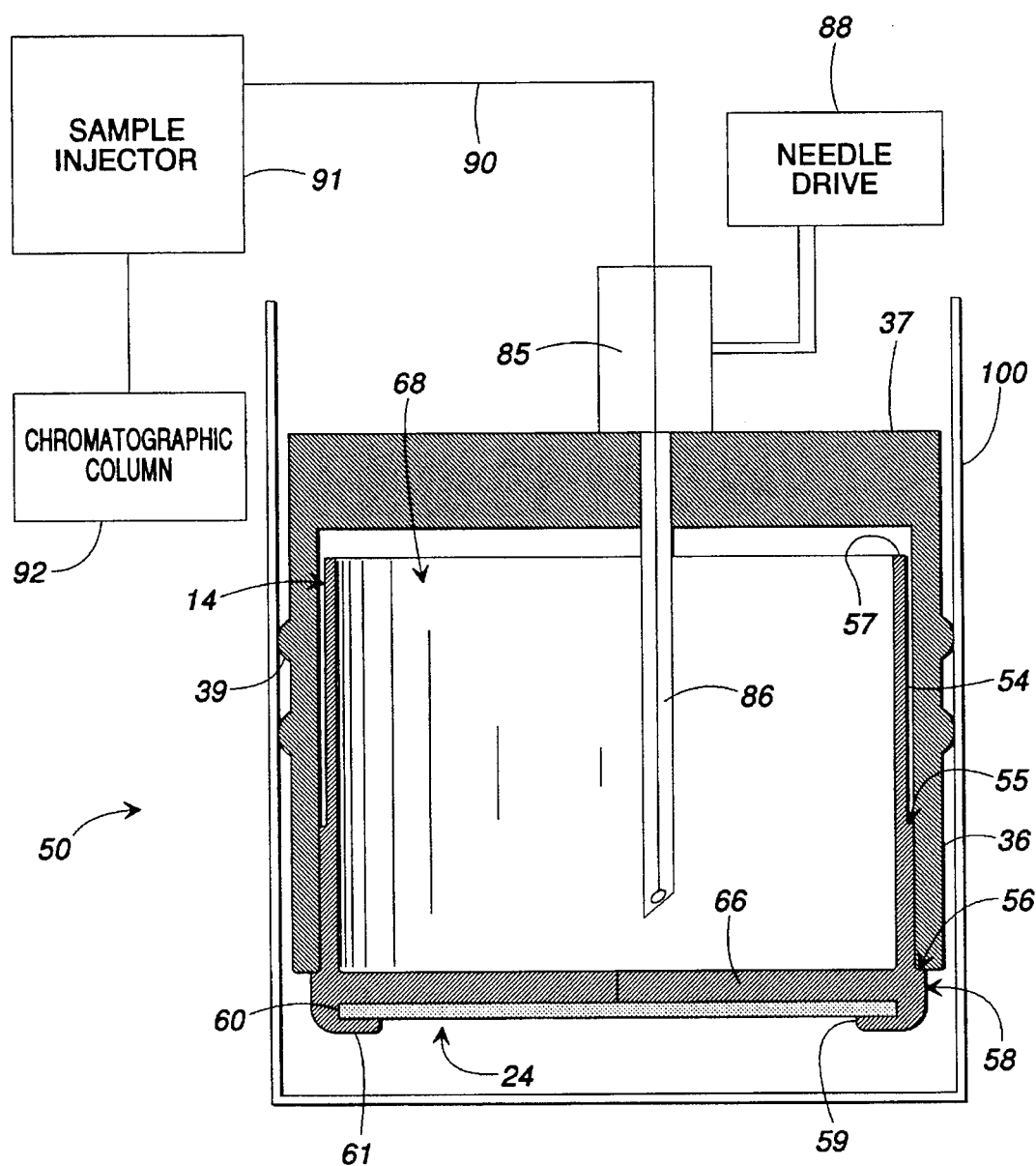
FIG. 7 is a side cross sectional view of the embodiment of FIG. 4, with the filtering device assembled and positioned within a vial, and showing diagramatically a needle drive mechanism and connection to an analyzer.

The filter receptacle 11 includes a housing 13 that is defined by an annular wall 14 such that the receptacle 11 can be slidably received by a vial 100 containing unfiltered sample, as shown in FIG. 7 or FIG. 8. The housing is molded in a conventional manner from a plastic material such as polypropylene or teflon. FIG. 1 shows a ridge or fin 16 which is provided around the outer wall of the filter receptacle 11. The ridge 16 is used to seal the filter receptacle 11 against the inside surface of the cap 12 in a manner described below. The ridge 16 preferably is integrally formed of the material of the wall 14, but may be any type of sealing ring which is typically used for sealing between similarly shaped members, such as a rubber O-ring. The annular wall 14 also defines an upstream end wall or enlarged diameter portion 15 at the filter end thereof for forming a shoulder 17 around the filter receptacle 11.

The annular wall 14 terminates in a filter mounting opening 18 such that the upstream end wall enclosed the upstream end of the housing and defines the filter mounting opening therethrough that is larger in area than a filtered liquid opening 30 in a partition 28 for receiving the liquid sample flow from the vial. An annular filter-holding recess 20 is formed in the annular wall 14 just inside the bottom end of the annular wall. A disc-shaped microporous membrane filter element 24 is sealed into the annular recess 20. The filter 24 may be of single or multiple layer construction and can be any type of filter media which is known in the art, such as polypropylene, paper, cellulose or glass fiber. The filter 24 may also be a combination of more than one filtration layer or surface. For instance, multiple filtration surfaces could be used when one surface is designed to prevent certain ions from being filtered or to pass certain ions, and another surface excludes particulate matter from being filtered. Ion exchange filters are well known in the art. Preferably the filter 24 is a single layer microporous membrane made from polypropylene. The filter 24 is preferably thin so as to limit its volume and capability of retaining a significant amount of sample. The porosity of the filter 24 is preferably between 0.1 and 1.0 microns, depending on the nature of the sample.

Installation of the filter 24 is completed by using a heat sealing technique to form a lip 21 over the edge of the filter 24. The heat also causes the filter material to form a heat seal bond with the material of the receptacle 11.

Immediately above the annular recess 20, a plurality of support ribs 26 extend from the annular wall 14 toward the center of the housing 13, terminating at a point spaced radially outwardly from the center. The ribs 26 contact the downstream side of the filter 24 to support it against pressure exerted on the upstream side. A partition or cover sheet 28 lies over the ribs 26 and fills the cross section of the housing with the exception of a central circular opening 30. As best seen in FIG. 3, a filtering chamber 32 is formed between the filter 24 and the cover sheet 28, and is interrupted only by the support ribs 26. Thus, liquid passing through the filter 24 may collect in the filtering chamber 32 and then pass into a removal chamber 34 consisting of the remainder of the housing 13 above the cover 28. The annular wall 14 terminates at its downstream end at a horizontal annular edge 35.

To maximize the volume of the filtering chamber 32, the number and size of the support ribs is kept small. In the embodiment shown in FIGS. 1 and 2, four support ribs are shown, terminating at the central opening 30. The positioning of the support ribs 26 in the preferred embodiment is shown in FIG. 2, a top view taken substantially along the line 2—2 of FIG. 1, just above the cover 28. The support ribs, shown in dashed lines in FIG. 2, may be integrally molded with the housing 13 and cover sheet 28. For some needs, the filter media support may also be a metal or rigid plastic material, such as polypropylene, having an array of small openings. The openings may be perforated or may be molded in a grid-like structure.

FIG. 1 shows the cap 12 positioned slightly spaced apart from engagement with the filter receptacle 11. The cap 12 includes an annular wall 36 enclosed at its top (the downstream end of the filtering device 10) by a septum 37. The septum 37 can be of any type known in the art which may be pierced by a conventional needle. Preferably, the septum 37 is simply a wall molded integrally with the rest of the cap 12, which may be formed of low density polyethylene (LDPE). A pair of sealing ridges 39 encircle the annular wall 36, which terminates at its upstream end in an annular edge 38.

FIG. 4 shows a longitudinal cross section of a second embodiment of a filter receptacle 50 according to the present invention. An annular wall 54 of the receptacle 50 is preferably staggered in thickness, increasing at a rounded shoulder 55 and at a sharper shoulder 56. Thus, the outer portion of the annular wall 14 has three separate exterior diameters, with the largest section 58 being adjacent to a filter-receiving opening 59. The shoulder 56 intersects the section 58 at approximately right angles and provides a flat bearing surface for receiving the annular edge 38 of the cap 12, as shown in FIG. 7. In contrast, the shoulder 55 is rounded to allow the annular edge to slide past during assembly of the two parts of the filtering device.

The filter 24 in the second embodiment is located and supported in a manner similar to that in the preferred embodiment described above. An annular recess 60 in the interior surface of the annular wall 54 receives the filter 24, between an annular lip 61 which extends inwardly a short distance to assure retention of the filter, and a cover sheet 62. The lip 61 and filter 24 are heat sealed in the manner described above in connection with the first embodiment. The cover sheet 62 defines a central opening 63, which is somewhat larger than the opening 30 of the first embodiment. A plurality of support ribs 66 extend across the receptacle 50. The eight ribs 66, shown best in FIGS. 5 and 6, are connected at the center of the filter receptacle 50. A large filtering surface area is exposed while providing the support needed in order to maintain the filter 24 in place over the bottom opening 59 of the filter receptacle 50. In a manner similar to that of the first embodiment, a filtering chamber 67 is formed between the filter 24 and the cover sheet 62, and is interrupted only by the support ribs 66. Thus, liquid passing through the filter 24 may collect in the filtering chamber 67 and then pass into a removal chamber 68 consisting of the remainder of the filter receptacle 50 above the cover 62.

The filter receptacle 50 is used in conjunction with a cap 12 identical to that shown in FIG. 1. In the case of both of the foregoing embodiments, the cap 12 is assembled with the filter receptacle 11 or 50 prior to insertion into a vial. Referring to FIG. 7, the filter receptacle 50 is slid into the cap 12 until the annular edge 38 of the cap slides over the rounded shoulder 55 and then abuts the flat shoulder 56. In this configuration, the annular wall of the receptacle 50 between shoulders 55 and 56 is pressed against the inner surface of the cap wall 36 to form a liquid-tight seal.

In the case of the first embodiment, the assembly (not shown) is similar, but the cap 12 slides over the annular wall 14 and over the ridge 16 prior to abutting the shoulder 17. The seal between the filter receptacle 11 and the cap 12 is formed by the ridge 16.

In operation of either of the above embodiments, first a quantity of sample is placed into the vial 100, and an assembled filter device 10' is slid into the vial above the sample, with the annular wall 36 of the cap 12 in sealing relationship with the interior surface of the vial to prevent liquid from extruding between the vial 100 and the outer wall of the filtering device. In the first embodiment, the wall 36 is pressed against the vial and the ridge 16 is pressed against the internal surface of the wall 36. This prevents liquid from passing upward between the filtering device 10' and the vial. In the second embodiment, the wall 36 is pressed against the vial between the shoulders 55 and 56 of the receptacle wall 54 to prevent liquid from passing upward between the filtering device 10' and the vial.

The vial then is inserted into position in a sample handling device such as an autosampler. The sample handling device includes a needle housing 85 from which extends a hollow needle 86. The needle housing 85 is connected to a drive mechanism 88 which moves the needle up and down. The drive mechanism may operate using a gear drive, a hydraulic or pneumatic drive, or other conventional means. A fluid line 90 connects the interior of the hollow needle 86 to a sample injection port 91, which then directs the sample to the analyzer, such as a chromatographic column 92. A sampling handling device suitable for use with the present invention is disclosed in U.S. Pat. No. 3,918,913, which is incorporated by reference herein in its entirety.

When a signal is received from the analyzer connected to the sampling handling device instructing the device to deliver a sample to the analyzer, the drive mechanism 88 moves the needle housing 85 downward until the needle 86 pierces the septum 37 and the housing 85 contacts the septum 37. Thus, the needle extends well into the removal chamber. Further downward movement of the needle housing 85 forces the cap and receptacle down into the vial until the filter 24 reaches the liquid sample in the vial.

The piston action of the filtration device forces the liquid up through the filter and into the space between the support ribs 26 or 66. As the open cross sectional area of the filter 24 is large, the filtration occurs quickly and efficiently. Furthermore, as the filter is thin, little sample material is retained within the filter. When the sample fills the space between the ribs, it moves upwardly into the removal chamber through the central opening 30 or 63.

It should be understood that the speed of travel of the filtration device into the vial may be controlled depending on the porosity or transfer characteristics of the filter material.

Only filtered sample can enter the hollow needle 86. Filtered sample can be removed from the filtering receptacle using either positive or negative displacement. Using positive displacement, filtered sample can be removed by forcing sample into the hollow needle 86 and into the analyzer injection port 91 by the pressure exerted on the sample through the force applied to the descending filtering receptacle. On the other hand, filtered sample may also be removed by sending a command to apply suction to draw the liquid from the filtering device into the analyzer injection port 91. In simpler devices, the sample could be drawn directly into an analytical chamber or cell.

FIG. 8 is a cross sectional view of a third embodiment of a filter receptacle 70 according to the present invention used in a sample removal and delivery system 71. Rather than having an annular wall, the receptacle 70 is a block of plastic material in which is formed a filter-receiving opening 72 at the upstream end, a conical removal chamber 74 at the downstream end, and a narrow well 76 leading from the chamber 74 toward the opening 72.

The filter 24 is located in the opening 72 in a recess 78 formed below the well 76. The recess 78 has an undercut annular side wall 80 and a plurality of support ribs 82 which, like the ribs 26 of the first embodiment, extend radially inwardly and stop at the diameter of the well 76. The filter 24 fits into the recess 78 and is pressed against the ribs 82 by the undercut wall 80. A plenum or filtering chamber is thus formed between the filter and the body of the receptacle 70 in the spaces between the ribs 82. This embodiment provides a means for efficient sample removal because the well 76 provides a deep volume of sample, even if the amount of sample is small.

In the embodiment of FIG. 8, the filtering receptacle 70 defines two sealing ridges 84 around the outer wall of the filtering receptacle 70 to seal the filtering receptacle 70 against the inner surface of the vial 100. At the top of the conical chamber 74 there is an annular edge 75. Again, the cap 12 may be identical to that used in connection with the other embodiments.

In FIG. 8, the cap 12 and filter receptacle 70 are shown inserted in a vial 100. The annular edge 38 of the cap abuts the edge 75 of the receptacle 70 to effectively protect any sample in the receptacle. The use and operation of the third embodiment of the invention is basically similar to that of the other embodiments as described above. Rather than assembling the filter receptacle and cap before insertion into the vial, the receptacle is slid into the vial, and then a sealing cap 12 is slid into the vial above the receptacle. When the needle 86 is inserted through the septum 37, it preferably extends deep into the well 76. As the parts are forced downward, the liquid after passing through the filter first fills the well 76 and then begins to fill the conical chamber 74.

Figure 11:
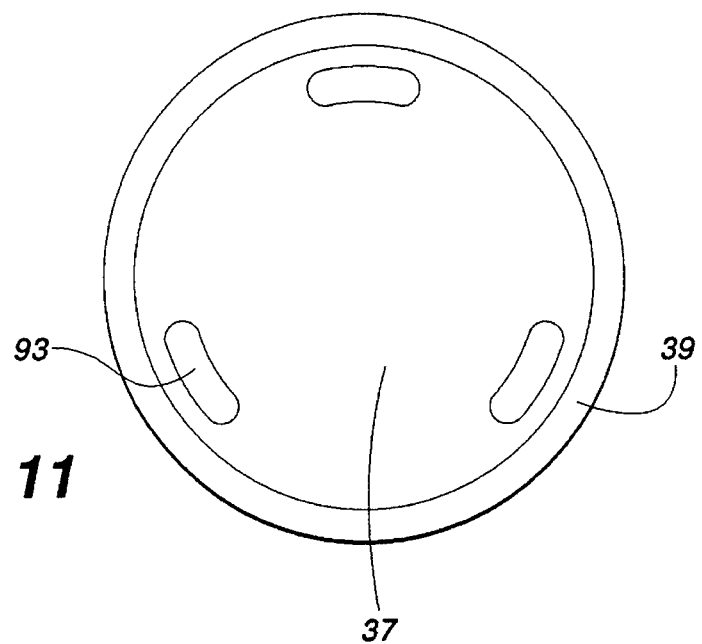
FIG. 11 is a top view of the two-part filtration device used in the sample removal and delivery system of FIG. 9.

FIG. 9 is an exploded side view of another embodiment of a sample removal and delivery system 101 according to the present invention. The system 101 uses negative displacement sample removal, in a manner known to those skilled in the art. A modified, two-part filtration device 10' is placed inside a vial 100 containing sample such that the wall 36 of the filtration device is pressed against the vial to prevent liquid from passing upward between the filtering device 10' and the vial 100. In this embodiment, the septum device 37 has a plurality of holes 93 formed in it, shown in FIG. 11. The holes 93 permit the liquid sample to flow through the filtering device 10' and upward into the vial 100 as described below.

A needle 105 of a negative displacement sample removal system is positioned above the vial 100. As such needles often do not have a needle housing suitable for engaging and driving the filtration device 10', a collar 106 is attached around the needle 105 at a position spaced apart from the tip of the needle.

A protective cap 102 of the type typically used in negative displacement sample removal systems is provided to enclose the vial 100 after insertion of the filtration device 10'. The top of the cap 102 is formed as a septum or cover that can be pierced by the needle 105 and also penetrated by the collar 106. The septum may be made of a rubber membrane, Teflon, or plastic material.

Figure 10:
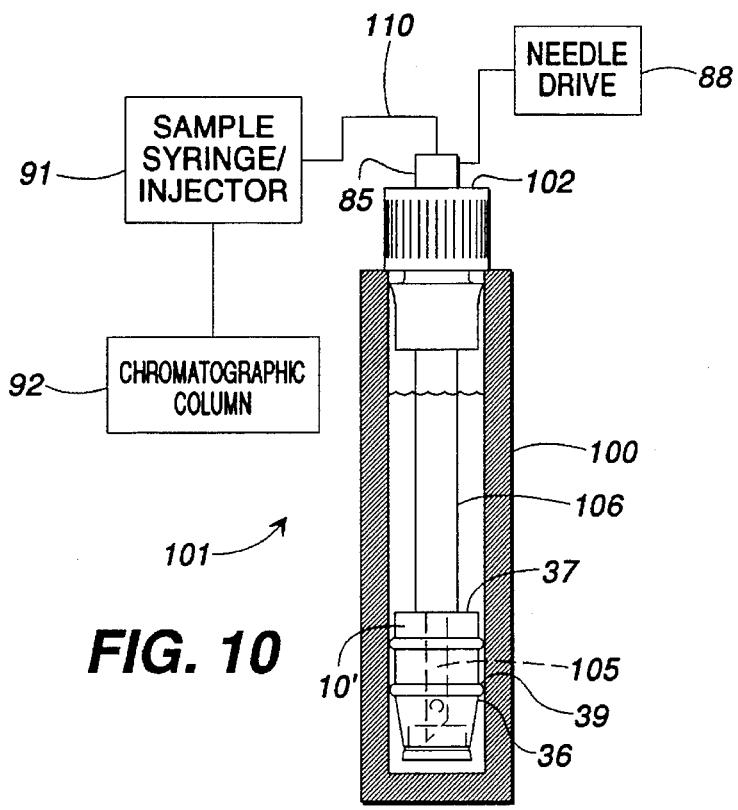
FIG. 10 is a side cross sectional view of the sample removal and delivery system of FIG. 9, showing the needle and filtration device in a fully inserted position.

In operation, the needle 105 and needle collar 106 are driven downward such that both pierce the vial septum device 102 and descend into the vial as shown in FIG. 10. The needle 105 pierces the septum device 37, which has at least one hole 93 in it to permit filtered sample to flow out of the top of the filtering device, and the needle collar 106 forces the filtration device 10' downward into the vial. The holes 93 are positioned at a distance from the center of the septum 37 greater than the radius of the collar 106. Filtered sample can then be removed from the filtration device and the vial along a line 110 using negative pressure generated by a syringe or suction pump in a sample syringe/injector component 111 of the negative displacement system.

On the one hand, this embodiment provides the additional advantage of being able to obtain large sample quantities due to the larger filtered sample storage area created by the holes 93 in the filtering device septum 37. On the other hand, this embodiment enables filtration in a negative displacement sample removal system, so that very small samples can be withdrawn by suction from within the filtration device 10'.

In summary, In the case of small samples, the structure of the filter receptacles of the present invention allows the use of a thin filter and efficiently moves sample within range of the hollow needle without retaining too much of the sample within the filter. In extreme cases of very small samples, the embodiment including the well 76 contains the sample in a volume shaped for efficient removal of a large proportion of the filtered sample, leaving even less waste behind.

It will also be seen that a filtering device embodying the present invention protects the sample from the environment by providing a non-porous septum that is not pierced until the sample is needed and fits tightly around the needle which withdraws the sample. Also, the slidably sealed or abutting edges of the cap and receptacle effectively seal the interior of the filtering device. Furthermore, the design of the filtering device allows filtering and delivery of the sample to be accomplished fully automatically under control of the analyzer, without the problems associated with prior automatic devices.

While this invention has been described in detail with particular reference to a preferred embodiment thereof, it will be understood that variations and modifications can be made without departing from the spirit and scope of the invention as described hereinbefore and as defined in the following claims.

What is claimed is:

1. A filtering receptacle shaped to be slidably received by a vial, for use in filtering and receiving a liquid sample initially contained in said vial, comprising:

a hollow housing having an upstream end and a downstream end opposite the upstream end for receiving a flow of the liquid sample from the vial, the hollow housing shaped to be slidably received by a vial in liquid sealing engagement with an interior surface of said vial;

an upstream end wall enclosing the upstream end of said housing and defining a filter mounting opening therethrough for receiving the liquid sample flow from the vial, so that the flow of the liquid sample flows from the vial, through the filter mounting opening in the upstream end wall, and toward the downstream end of the housing when the hollow housing is slidably received by the vial;

a filter having a downstream surface mounted to enclose said filter mounting opening with the downstream surface of the filter facing the downstream end of the housing;

at least one support rib positioned within said housing to engage a portion of the downstream surface of said filter; and a downstream end wall enclosing the downstream end of the housing comprising a septum pierceable by a needle which receives the flow of liquid sample from the hollow housing, wherein said housing comprises two parts, a filter receptacle including said upstream end wall and said filter, and a peripheral receptacle wall shaped to be slidably received by said vial in liquid sealing engagement with the interior surface of said vial, said peripheral receptacle wall defining a downstream facing shoulder; and a cap including said downstream end wall and a peripheral cap wall shaped to be slidably received by said vial in liquid sealing engagement with the interior surface of said vial, said peripheral cap wall extending from the downstream end wall to an upstream facing peripheral edge;

said peripheral cap wall fitting over said peripheral receptacle wall with said upstream facing peripheral edge abutting said downstream facing shoulder such that said peripheral cap wall is pressed against the interior surface of said vial.

2. A filtering receptacle shaped to be slidably received by a vial, for use in filtering and receiving a liquid sample initially contained in said vial, comprising:

a hollow housing having an upstream end and a downstream end opposite the upstream end for receiving a flow of the liquid sample from the vial, the hollow housing shaped to be slidably received by a vial in liquid sealing engagement with an interior surface of said vial, said housing having a longitudinal axis extending from said upstream end to said downstream end;

a partition positioned within said housing to divide said housing into a filter chamber and a removal chamber, said partition defining a filtered liquid opening therethrough and defining an upstream surface facing axially towards the upstream end of said housing;

an upstream end wall enclosing the upstream end of said housing and defining a filter mounting opening therethrough larger in area than said filtered liquid opening for receiving the liquid sample flow from the vial, so that the flow of the liquid sample flows from the vial, through the filter mounting opening in the upstream end wall, and toward the downstream end of the housing when the hollow housing is slidably received by the vial, the filter chamber positioned between the partition and the upstream end wall;

a filter having a downstream surface and attached to said upstream end wall enclosing said filter mounting opening with the downstream surface of the filter facing the downstream end of the housing;

a downstream end wall enclosing the downstream end of the housing comprising a septum pierceable by a needle, the removal chamber positioned between the partition and the downstream end wall; and at least one support rib positioned within the filter chamber positioned axially between the upstream surface of the partition and the downstream surface of said filter to supportingly engage a portion of the downstream surface of said filter.

3. The receptacle of claim 2, further comprising a well formed directly down of stream said filtered liquid opening, said well having a cross sectional area smaller than the cross sectional area of said housing.

4. A filtering receptacle shaped to be slidably received by a vial, for use in filtering and receiving a liquid sample initially contained in said vial, comprising:

a hollow housing having an upstream end and a downstream end opposite the upstream end for receiving a flow of the liquid sample from the vial, the hollow housing shaped to be slidably received by a vial in liquid sealing engagement with an interior surface of said vial;

a partition positioned within said housing to divide said housing into a filter chamber and a removal chamber, said partition defining a filtered liquid opening therethrough;

an upstream end wall enclosing the upstream end of said housing and defining a filter mounting opening therethrough larger in area than said filtered liquid opening for receiving the liquid sample flow from the vial, so that the flow of the liquid sample flows from the vial, through the filter mounting opening in the upstream end wall, and toward the downstream end of the housing when the hollow housing is slidably received by the vial, the filter chamber positioned between the partition and the upstream end wall;

a filter having a downstream surface and attached to said upstream end wall enclosing said filter mounting opening with the downstream surface of the filter facing the downstream end of the housing;

at least one support rib positioned within said housing to engage a portion of the downstream surface of said filter; and a downstream end wall enclosing the downstream end of the housing comprising a septum pierceable by a needle which receives the flow of liquid sample from the hollow housing, the removal chamber positioned between the partition and the downstream end wall, wherein said support rib extends from said partition to said upstream end wall.

5. The receptacle of claim 4 further comprising a plurality of support ribs positioned within said housing to engage a portion of the downstream surface of said filter, said support ribs extending radially towards the center of said filter from a peripheral wall of said housing and extending from said partition to said upstream end wall.

6. A filtering receptacle shaped to be slidably received by a vial, for use in filtering and receiving a liquid sample initially contained in said vial, comprising:

a hollow housing having an upstream end and a downstream end opposite the upstream end for receiving a flow of the liquid sample from the vial, the hollow housing shaped to be slidably received by a vial in liquid sealing engagement with an interior surface of said vial;

a partition positioned within said housing to divide said housing into a filter chamber and a removal chamber, said partition defining a filtered liquid opening therethrough;

an upstream end wall enclosing the upstream end of said housing and defining a filter mounting opening therethrough larger in area than said filtered liquid opening for receiving the liquid sample flow from the vial, so that the flow of the liquid sample flows from the vial, through the filter mounting opening in the upstream end wall, and toward the downstream end of the housing when the hollow housing is slidably received by the vial, the filter chamber positioned between the partition and the upstream end wall;

a filter having a downstream surface and attached to said upstream end wall enclosing said filter mounting opening with the downstream surface of the filter facing the downstream end of the housing; and a downstream end wall enclosing the downstream end of the housing comprising a septum pierceable by a needle which receives the flow of liquid sample from the hollow housing, the removal chamber positioned between the partition and the downstream end wall wherein said housing comprises two parts, a filter receptacle including said upstream end wall, said filter and said partition, and a peripheral receptacle wall shaped to be slidably received by said vial in liquid sealing engagement with the interior surface of said vial, said peripheral receptacle wall defining a downstream facing shoulder; and a cap including said downstream end wall and a peripheral cap wall shaped to be slidably received by said vial in liquid sealing engagement with the interior surface of said vial, said peripheral cap wall extending from the downstream end wall to an upstream facing peripheral edge;

said peripheral cap wall fitting over said peripheral receptacle wall with said upstream facing peripheral edge abutting said downstream facing shoulder such that said peripheral cap wall is pressed against the interior surface of said vial.

7. A sample removal and delivery system, comprising:

a vial for containing a liquid sample;

a housing having an upstream end and a downstream end opposite the upstream end for receiving a flow of the liquid sample from the vial, the housing shaped to be slidably received by said vial in liquid sealing engagement with an interior surface of said vial;

an upstream end wall at the upstream end of said housing defining a filter mounting opening therethrough for receiving the liquid sample flow from the vial, so that the flow of the liquid sample flows from the vial, through the filter mounting opening in the upstream end wall, and toward the downstream end of the housing when the housing is slidably received by the vial;

a filter having a downstream surface mounted to enclose said filter mounting opening with the downstream surface of the filter facing the downstream end of the housing;

a downstream end wall enclosing the downstream end of the housing comprising a septum;

a needle for receiving the flow of the liquid sample from the housing mounted in a needle housing shaped to engage said downstream end wall; and a needle drive mechanism operable to move said needle through said septum and to move said housing into said vial upon engagement of said needle housing with said downstream end wall, such that liquid is forced through said filter into said housing.

8. The system of claim 7, wherein said downstream end wall includes at least one hole permitting liquid flow through said downstream wall.

9. The system of claim 8, further comprising a pierceable vial cap enclosing said vial.

10. The system of claim 9, further comprising a collar positioned around said needle spaced away from a point of said needle, said collar positioned to pass through said vial cap and engage said downstream end of said housing.

11. The system of claim 8, further comprising a partition positioned within said housing to divide said housing into a filter chamber and a removal chamber, said partition defining a filtered liquid opening therethrough smaller in area than said filter mounting opening.

12. The system of claim 11, further comprising at least one support rib positioned within said housing to engage a portion of the downstream surface of said filter.

13. The system of claim 7, further comprising a partition positioned within said housing to divide said housing into a filter chamber and a removal chamber, said partition defining a filtered liquid opening therethrough smaller in area than said filter mounting opening.

14. The system of claim 13, wherein said support rib extends from said partition to said upstream end wall.

15. The system of claim 7, further comprising a plurality of support ribs positioned within said housing to engage a portion of the downstream surface of said filter, said support ribs extending radially from a peripheral wall of said housing toward the center of said filter to and extending from said partition to said upstream end wall.

16. The system of claim 7, further comprising at least one support rib positioned within said housing to engage a portion of the downstream surface of said filter.

17. The system of claim 7, wherein said housing comprises two parts, a filter receptacle including said upstream end wall and said filter, and a peripheral receptacle wall shaped to be slidably received by said vial in liquid sealing engagement with the interior surface of said vial, said peripheral receptacle wall defining a downstream facing shoulder; and a cap including said downstream end wall and a peripheral cap wall shaped to be slidably received by said vial in liquid sealing engagement with the interior surface of said vial, said peripheral cap wall extending from the downstream end wall to an upstream facing peripheral edge;

said peripheral cap wall fitting over said peripheral receptacle wall with said upstream facing peripheral edge abutting said downstream facing shoulder such that said peripheral cap wall is pressed against the interior surface of said vial.

\* \* \* \* \*